US012076549B2

(12) United States Patent
Stotz et al.

(10) Patent No.: US 12,076,549 B2
(45) Date of Patent: Sep. 3, 2024

(54) FEED LINE FOR A PUMP UNIT OF A CARDIAC ASSISTANCE SYSTEM, CARDIAC ASSISTANCE SYSTEM AND METHOD FOR PRODUCING A FEED LINE FOR A PUMP UNIT OF A CARDIAC ASSISTANCE SYSTEM

(71) Applicant: KARDION GMBH, Stuttgart (DE)

(72) Inventors: Ingo Stotz, Ditzingen (DE); Fabian Eiberger, Gerlingen (DE); Peter Wassermann, Weil der Stadt (DE)

(73) Assignee: KARDION GMBH, Stuttgart (DE)

( * ) Notice: Subject to any disclaimer, the term of this patent is extended or adjusted under 35 U.S.C. 154(b) by 878 days.

(21) Appl. No.: 17/261,335

(22) PCT Filed: Jul. 19, 2019

(86) PCT No.: PCT/EP2019/069571
§ 371 (c)(1),
(2) Date: Jul. 19, 2021

(87) PCT Pub. No.: WO2020/016438
PCT Pub. Date: Jan. 23, 2020

(65) Prior Publication Data
US 2021/0339005 A1 Nov. 4, 2021

(30) Foreign Application Priority Data
Jul. 20, 2018 (DE) .......................... 102018212153.2

(51) Int. Cl.
*A61M 60/237* (2021.01)
*A61M 60/178* (2021.01)
(Continued)

(52) U.S. Cl.
CPC ........ *A61M 60/237* (2021.01); *A61M 60/178* (2021.01); *A61M 60/183* (2021.01); *A61M 60/174* (2021.01); *A61M 2207/00* (2013.01)

(58) Field of Classification Search
CPC ............ A61M 60/237; A61M 2207/00; A61M 2206/10; A61M 2206/20
See application file for complete search history.

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| AU | 7993698 | 2/1999 |
| AU | 2002308409 | 12/2005 |

(Continued)

OTHER PUBLICATIONS

International Search Report and Written Opinion received in PCT Application No. PCT/EP2019/069571, dated Sep. 24, 2019 in 15 pages.

(Continued)

*Primary Examiner* — Catherine M Voorhees
(74) *Attorney, Agent, or Firm* — Knobbe, Martens, Olson & Bear, LLP

(57) ABSTRACT

The invention relates to a feed line (105) for a pump unit (110) of a cardiac support system (100). The feed line (105) is embodied to guide a fluid flow to a pump unit (110) of the cardiac support system (100). The feed line (105) comprises a feed head portion (130) with at least one introduction opening (140) for introducing the fluid flow into the feed line (105) and a contoured portion (135) with an inner surface contour. The contoured portion (135) is disposed adjacent to the feed head portion (130). An inner diameter of the contoured portion (135) at a first position is greater than the inner diameter at a second position. The inner surface contour has a rounded portion at the second position for reducing the inner diameter.

12 Claims, 5 Drawing Sheets

(51) Int. Cl.
*A61M 60/183* (2021.01)
*A61M 60/174* (2021.01)

(56) References Cited

U.S. PATENT DOCUMENTS

| | | |
|---|---|---|
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A * | 6/1999 | Siess ............ F04D 29/047 |
| | | 600/16 |
| 5,921,913 A | 7/1999 | Siess |
| 5,964,694 A | 10/1999 | Siess et al. |
| 6,001,056 A | 12/1999 | Jassawalla et al. |
| 6,007,478 A * | 12/1999 | Siess ............ A61M 25/0053 |
| | | 600/585 |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,011,620 B1 | 5/2006 | Siess |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,699,586 B2 | 4/2010 | LaRose et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |
| 7,972,122 B2 | 7/2011 | LaRose et al. |
| 7,998,190 B2 | 8/2011 | Gharib et al. |
| 8,007,254 B2 | 8/2011 | LaRose et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |

(56) References Cited

U.S. PATENT DOCUMENTS

| | | |
|---|---|---|
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,668,473 B2 | 3/2014 | LaRose et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,790,236 B2 | 7/2014 | LaRose et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,339,598 B2 | 5/2016 | LaRose et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,737,652 B2 | 8/2017 | LaRose et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,985 B2 | 4/2019 | Larose et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |

(56) References Cited

U.S. PATENT DOCUMENTS

| | | |
|---|---|---|
| 10,814,053 B2 | 10/2020 | Throckmorton et al. |
| 10,857,273 B2 | 12/2020 | Hodges et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |

(56) References Cited

U.S. PATENT DOCUMENTS

| | | |
|---|---|---|
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,746,906 B1 | 9/2023 | Balta et al. |
| 11,754,075 B2 | 9/2023 | Schuelke et al. |
| 11,754,077 B1 | 9/2023 | Mohl |
| 11,759,622 B2 | 9/2023 | Siess et al. |
| 11,781,550 B2 | 10/2023 | Siess et al. |
| 11,804,767 B2 | 10/2023 | Vogt et al. |
| 11,806,116 B2 | 11/2023 | Tuval et al. |
| 11,833,278 B2 | 12/2023 | Siess et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0044266 A1 | 3/2004 | Siess et al. |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0138080 A1 | 5/2009 | Siess et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0298625 A1 | 11/2010 | Reichenbach et al. |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0107399 A1* | 4/2014 | Spence .............. A61M 60/857 600/16 |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-Hardt et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |

(56) References Cited

U.S. PATENT DOCUMENTS

| | | |
|---|---|---|
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1* | 9/2019 | Judisch ............... A61M 60/861 |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0407403 A1 | 12/2022 | Vogt et al. |
| 2023/0001178 A1 | 1/2023 | Corbett et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |

(56) References Cited

FOREIGN PATENT DOCUMENTS

| | | |
|---|---|---|
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 201150675 | 11/2008 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 101 55 011 | 11/2005 |
| DE | 601 19 592 | 9/2006 |
| DE | 20 2005 020 288 | 6/2007 |
| DE | 10 2008 060 357 | 6/2010 |
| DE | 10 2009 039 658 | 3/2011 |
| DE | 20 2009 018 416 | 8/2011 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 3 127 562 | 2/2017 |
| EP | 2 585 129 | 3/2017 |
| EP | 3 143 682 | 3/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 2 344 218 | 4/2021 |
| EP | 3 436 104 | 4/2021 |
| EP | 3 749 383 | 4/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |

(56) References Cited

FOREIGN PATENT DOCUMENTS

| | | |
|---|---|---|
| EP | 3 216 467 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 3 795 208 | 10/2023 |
| EP | 4 149 606 | 10/2023 |
| EP | 3 157 596 | 11/2023 |
| EP | 4 061 470 | 11/2023 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515375 | 9/2001 |
| JP | 2003-019197 | 1/2003 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6267625 | 1/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |

(56) References Cited

FOREIGN PATENT DOCUMENTS

| | | |
|---|---|---|
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/088939 | 3/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

International Preliminary Report on Patentability and Written Opinion received in PCT Application No. PCT/EP2019/069571, dated Oct. 30, 2020 in 23 pages.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.

* cited by examiner

FEED LINE FOR A PUMP UNIT OF A CARDIAC ASSISTANCE SYSTEM, CARDIAC ASSISTANCE SYSTEM AND METHOD FOR PRODUCING A FEED LINE FOR A PUMP UNIT OF A CARDIAC ASSISTANCE SYSTEM

BACKGROUND

Field

The invention relates to a feed line for a pump unit of a cardiac support system, a cardiac support system and method for producing a feed line for a pump unit of a cardiac support system.

Description of the Related Art

A heart pump may include a pump unit and an inlet hose for supplying a blood flow to the pump unit. The heart pump may further include a structure to prevent or reduce blood damage (hemolysis) in the region of the pump unit. US 2017/087288 A1 describes a pump unit having a trumpet-shaped enlargement of a length of the pump unit in order to reduce hemolysis and/or minimize pressure loss.

SUMMARY

Based on this, the underlying object of the invention is to further improve the systems and methods known in the state of the art while ensuring the highest possible pumping efficiency with a compact design.

With this in mind, the approach presented here introduces a feed line for a pump unit of a cardiac support system, a cardiac support system and a method for producing a feed line for a pump unit of a cardiac support system. Advantageous further developments and improvements of the device are described herein.

This approach presents a design for a feed line for a pump unit of a cardiac support system, which sets a flow behavior of a fluid flow introduced into the feed line by means of an inner surface contour in a section near an inlet of the feed line. Flow separation of the fluid flow can advantageously be reduced or completely avoided with the aid of a rounded portion, for example a sectionally concave and additionally or alternatively convex configuration of the inner surface contour. The pressure loss when conducting the fluid flow in the feed line decreases along with the reduced or avoided flow separation, which is advantageous in terms of the power consumption of a pump unit and thus a pump efficiency of the cardiac support system. The reduction or avoidance of flow separation with the aid of the inner surface contour advantageously enables a compact design of the feed line, which is advantageous in particular for a cardiac support system for minimally invasive implantation, for example for transaortic or transfemoral implantation.

The invention presents a feed line for a pump unit of a cardiac support system. The feed line is configured to conduct a fluid flow to the pump unit of the cardiac support system. The feed line comprises at least one feed head portion and a contoured portion. The feed head portion comprises at least one introduction opening for introducing the fluid flow into the feed line. The contoured portion has an inner surface contour. The contoured portion is disposed adjacent to the feed head portion. An inner diameter of the contoured portion at a first position is greater than the inner diameter at a second position. The inner surface contour has a rounded portion at the second position for reducing the inner diameter.

The cardiac support system can be a heart pump, for example, such as a left ventricular support system, a right ventricular support system, or a biventricular support system. The cardiac support system can be designed for minimally invasive implantation, for example. The feed line can be configured as a flow channel for conducting a fluid flow. The feed line can also be configured as a hose. In the implanted state of the cardiac support system, the feed line can be configured to conduct a blood flow from a ventricle to the pump unit of the cardiac support system as the fluid flow. The pump unit can be a microaxial pump, for example. The feed head portion can be understood to be a subsection of the feed line disposed between a head unit of the cardiac support system, for example a sensor assembly, and a further subsection of the feed line disposed adjacent to the pump unit. The introduction opening can be cut out of the feed line, for example. The introduction opening can be configured as a multi-part window opening, for example by three windows cut into the feed line and rounded in the direction of the pump unit. The contoured portion can be understood to be a section of the feed line disposed between the feed head portion and the further subsection of the feed line. The inner surface contour can be an incised or applied structure, for example, or a predefined material configuration such as a sectionally different wall thickness, or an insertion element having a specific shape or structure. The first position can be upstream of the second position with respect to a flow direction of the fluid flow. The rounded portion of the inner surface contour can be a convex protrusion. The inner surface contour can also have a further rounded portion at the first position, for example in the form of a concave recess.

According to one embodiment, the inner diameter of the contoured portion at a third position can be greater than the inner diameter at the second position. The second position can be located between the third position and the first position, for example. The third position can therefore be downstream of the second position with respect to a flow direction of the fluid flow. The inner surface contour can also have a rounded portion in the form of a further concave recess at the third position, for example. This can advantageously change the flow behavior of the fluid flow, which reduces the flow separation of the fluid flow. This is advantageous for reducing pressure loss or friction of the fluid flow, which can increase the pump efficiency of the cardiac support system.

According to one embodiment, the first position can be disposed in the contoured portion between the feed head portion and the second position. The first position and the second position can be sections along a longitudinal axis of the contoured portion, for example. This arrangement advantageously allows the inner diameter of the contoured portion to be changed along the longitudinal axis of the contoured portion in order to set the flow behavior and with it the flow separation of the fluid flow by optimizing the configuration.

According to one embodiment, the first position and the second position can additionally or alternatively be disposed along the circumference of the contoured portion. A cross-section of the contoured portion can accordingly also have at least one rounded portion, as a result of which the flow behavior of the fluid flow can advantageously be set as well.

According to one embodiment, a length of the contoured portion can correspond to up to twice the inner diameter of the contoured portion. The length of the contoured portion can in particular correspond to a radius of the feed line within a tolerance range. The feed line can have a constant radius. The tolerance range can be understood to be a deviation of no more than twenty percent from the radius of the feed line, for example. A locally limited setting of the flow behavior is thus possible. Advantageously, the pressure loss further downstream of the feed line, i.e. in a subsection of the feed line between the contoured portion and the pump unit, is also lower, because the suppression of the separation results in lower turbulence of the fluid flow downstream.

According to one embodiment, an inner radius of the contoured portion at the second position can be at most one fifth smaller than the inner radius at the first position. This advantageously makes it possible to set the flow behavior and also conduct the fluid flow to be conveyed through the contoured portion without increasing the installation space.

The inner surface contour can furthermore be rotationally symmetrically formed. In the case of rotationally symmetrical inflow into the feed line, for example, this is advantageous to minimize flow separation and thus reduce pressure loss.

According to one embodiment, a wall thickness of the contoured portion at the first position can be less than the wall thickness at the second position. Alternatively or additionally, the inner surface contour can be configured as an insertion element of the contoured portion. Both embodiments advantageously enable a simple and cost-effective realization of the contoured portion.

Furthermore, according to one embodiment, at least one inlet edge of the introduction opening of the feed head portion can be rounded. This advantageously reduces pressure loss at the introduction opening.

According to one embodiment, the contoured portion can also have a constant outer diameter. This advantageously enables a compact design, which is advantageous in particular when using the feed line in conjunction with a cardiac support system for minimally invasive implantation.

The invention further presents a cardiac support system having an embodiment of the aforementioned feed line.

A method for producing a feed line for a cardiac support system is presented as well. The feed line is configured to conduct a fluid flow to a pump unit of the cardiac support system. The method includes a forming step. In the forming step, a feed head portion with at least one introduction opening for introducing the fluid flow into the feed line is formed. Furthermore, in the forming step, a contoured portion with an inner surface contour is formed, wherein the contoured portion is disposed adjacent to the feed head portion, wherein an inner diameter of the contoured portion at a first position is greater than the inner diameter at a second position and wherein the inner surface contour has a rounded portion at the second position for reducing the inner diameter.

The feed line can be cut out of a tube, for example, or the feed line can be configured as a hose and comprise an insertion element for configuring the contoured portion and the inner surface contour. An embodiment of the aforementioned sliding bearing device can advantageously be produced by carrying out the method.

BRIEF DESCRIPTION OF THE DRAWINGS

Design examples of the approach proposed here are shown in the drawings and explained in more detail in the following description. The figures show.

DETAILED DESCRIPTION

In the following description of favorable design examples of the present invention, the same or similar reference signs are used for elements shown in the various figures and having a similar effect; a repeated description of these elements is omitted.

Figure 1:
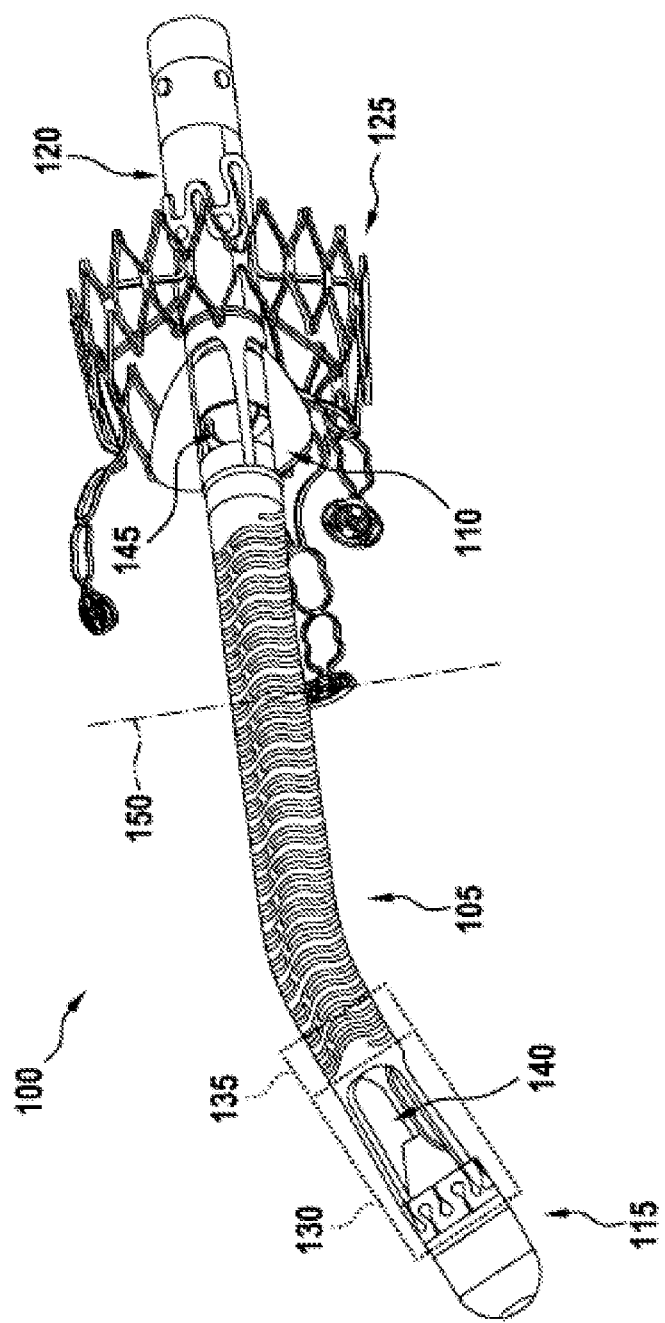
FIG. 1 a schematic illustration of a cardiac support system with a feed line.

FIG. 1 shows a schematic illustration of a cardiac support system 100 with a feed line 105 according to one design example. The figure shows a perspective view of the cardiac support system 100, which is exemplified as a left ventricular cardiac support system, left ventricular assist device (LVAD), for an aortic valve position. The elongated axial design of the cardiac support system 100 with a substantially constant outer diameter shown here enables transfemoral or transaortic implantation of the cardiac support system 100 for simple placement in a blood vessel, for example the aorta, by means of a catheter.

Corresponding to the configuration for the aortic valve position, the feed line 105 has an inclination or curvature of the longitudinal axis, for example, and thus a slightly curved shape. In addition to the feed line 105, the cardiac support system comprises a pump unit 110. A head unit 115 as well as a housing section 120 and an anchoring frame 125 are also shown as an example. The feed line 105 is disposed between the head unit 115 and the pump unit 110. The pump unit 110 is connected at an end facing away from the feed line 105 to the housing section 120 to which the anchoring frame 125 is attached.

According to one design example, the feed line 105 is configured to conduct a fluid flow to the pump unit 110 of the cardiac support system 100. The feed line comprises a feed head portion 130 and a contoured portion 135. The feed head portion 130 comprises at least one introduction opening 140 for introducing the fluid flow into the feed line 105. The contoured portion 135 has an inner surface contour. The contoured portion 135 is disposed adjacent to the feed head portion 130. Viewed in flow direction, the inner diameter of the contoured portion 135 at a first position is greater than the inner diameter at a second position. The inner surface contour has a rounded portion at the second position for reducing the inner diameter. Design examples of configurations of the contoured portion 135 are described with reference to the following FIGS. 2 to 9.

The feed head portion 130 and the contoured portion 135 are outlined in the design example shown here as an example. The contoured portion 135 in particular optionally covers a smaller or larger portion of the feed line 105 than shown here. In the implanted state of the cardiac support system 100, the feed head portion 130 and the contoured portion 135 are disposed in 20 the left ventricle. A further section of the feed line 105 is led through the aortic valve, and a section of the cardiac support system 100 with the pump unit 110 is disposed in a section of the aorta. A pump outlet 145 in the region of the pump unit 110 conducts the fluid flow conveyed through the feed line 105 into the aorta. As an example, the axis 150 shows a position of a heart valve, for example the aortic valve, through which the feed line 105 is passed in order to position the cardiac support system 100.

According to the design example shown here, at least one inlet edge of the introduction opening 140 of the feed head portion 130 is rounded. As an example, the introduction opening 140 here is configured as a window-shaped inlet cut into the feed head portion 130.

According to the design example shown here, a length of the contoured portion 135 corresponds to a radius of the feed line 105 within a tolerance range. The tolerance range is understood to be a deviation of no more than twenty percent from the radius of the feed line.

A cardiac support system which is limited in terms of installation space, such as the cardiac support system 100 shown here as an example, and can be implanted in a minimally invasive manner, has comparatively low power consumption at a given pump efficiency. The efficiency is limited by the friction in the pump of the pump unit 110. The pressure loss or friction in the feed line 105 as the fluid flow is conducted from the introduction opening 140 of the feed head portion 130 in the ventricle to the pump unit 110 can be adjusted via the configuration of the feed line 105. For this purpose, the inlet edges of the inlet opening 140 are rounded in order to reduce the pressure loss. This alone cannot prevent flow separation. Having an inlet inner surface contour in the form of the contoured portion 135 configured according to the approach presented here suppresses flow separation and consequently reduces pressure loss. Design examples of a correspondingly configured inlet inner surface contour are discussed in the following.

Figure 2:
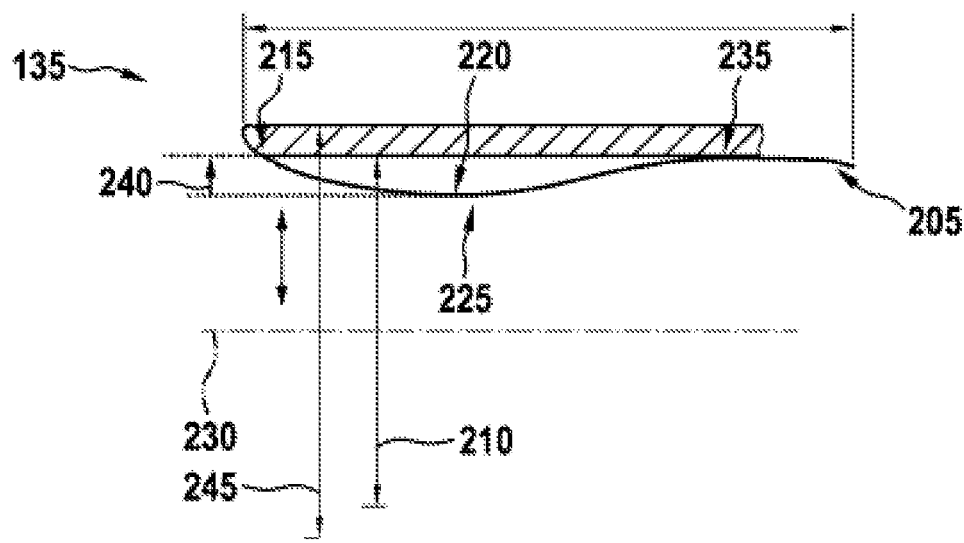
FIG. 2 a schematic illustration of part of a contoured portion of a feed line according to one design example.

FIG. 2 shows a schematic illustration of a part of a contoured portion 135 of a feed line according to one design example. The figure shows examples of dimensional relationships of the contoured portion 135 and the inner surface contour 205. The figure shows an axial section of a half of the contoured portion 135. The inner diameter 210 of the contoured portion 135 at a first position 215 is greater than the inner diameter 210 at a second position 220. To reduce the inner diameter 210, the inner surface contour 205 has a rounded portion 225 in the form of an axially arc-shaped inner wall profile at the second position 220. According to the design example shown here, the first position 215 indicates a location on the contoured portion 135 along a longitudinal axis of the contoured portion 135, and the second position 215 indicates a further location on the contoured portion 135 along the longitudinal axis. In the design example shown here, the longitudinal axis corresponds to an axis of rotation 230 of the contoured portion 135.

According to the design example shown here, the first position 215 is disposed in the contoured portion 135 between the feed head portion and the second position 220. With respect to a flow direction of the fluid flow introduced through the feed head portion and conducted in the direction of the pump unit through the feed line and thus through the contoured portion 135, the first position 215 is disposed upstream of the second position 220.

Furthermore, according to the design example shown here, the inner diameter of the contoured portion 135 at a third position 235 is greater than the inner diameter at the second position 220.

According to the design example shown here, an inner radius of the contoured portion 135 at the second position 220 is at most one fifth smaller than the inner radius at the first position 215. In the present FIG. 2 this is shown with the arrow 240, which indicates a fifth of the inner radius. The rounded portion 225 of the inner surface contour 205 is correspondingly configured at most as a convex protrusion in the range of up to a fifth of the inner radius, which is further visualized by the arrow 240.

According to one design example, the inner surface contour 205 is configured to be rotationally symmetrical. A part of the contoured portion 135 which is opposite to the part of the inner surface contour 205 shown here with respect to the axis of rotation 230 correspondingly has a rotationally symmetrically configured inner surface contour 205.

The configurations of the contoured portion 135 and the inner surface contour 205 shown here make it possible to reduce or suppress flow separations of the fluid flow in the feed line, which would otherwise develop downstream of the inlet edges. An outer diameter 245 of the contoured portion 135 remains constant and an enlargement of the installation space of the feed line is advantageously avoided. Using a design example of the contoured portion 135 shown here and the inner surface contour 205 reduces the pressure loss of the fluid flow to be conveyed. The inlet flows, and thus the flow behavior of the fluid flow, are directed only locally by the contoured portion 135. The contoured portion 135 optionally has a length that, in this design example, corresponds to at most twice the inner diameter of the feed line. Due to the configuration of the contoured portion 135, the pressure loss of the fluid flow further downstream is lower than in a feed line having a constant inner diameter without an inner surface contour, because a suppression or reduction of separation results in less turbulence downstream. The inner surface contour 205 is configured such that flow separation is largely suppressed over a length of up to four times the radius of the feed line. The local outer diameter 245 of the feed line is limited by a prescribed wall thickness. Adjacent to the introduction opening of the feed head portion, the inlet edge is convexly rounded to reduce flow separation. A configuration optimization of the inner surface contour 205, such as the configuration shown here, can be rotationally symmetrical or alternatively independent of the angle of rotation, as shown with reference to FIG. 8. According to the design example shown here, independent of the described inlet edge rounded portion, a contour profile of the inner surface contour 205 has two concave and one convex configuration optimization along with a constant wall thickness, as shown here with the aid of the first position 215, the second position 220, the third position 235 and the rounded portion 225. For this purpose, the wall inner contour is optionally configured such that locally a wall inner radius of up to four fifths with respect to the wall inner radius is achieved at a constant wall thickness of the contoured portion 135.

Figure 3:
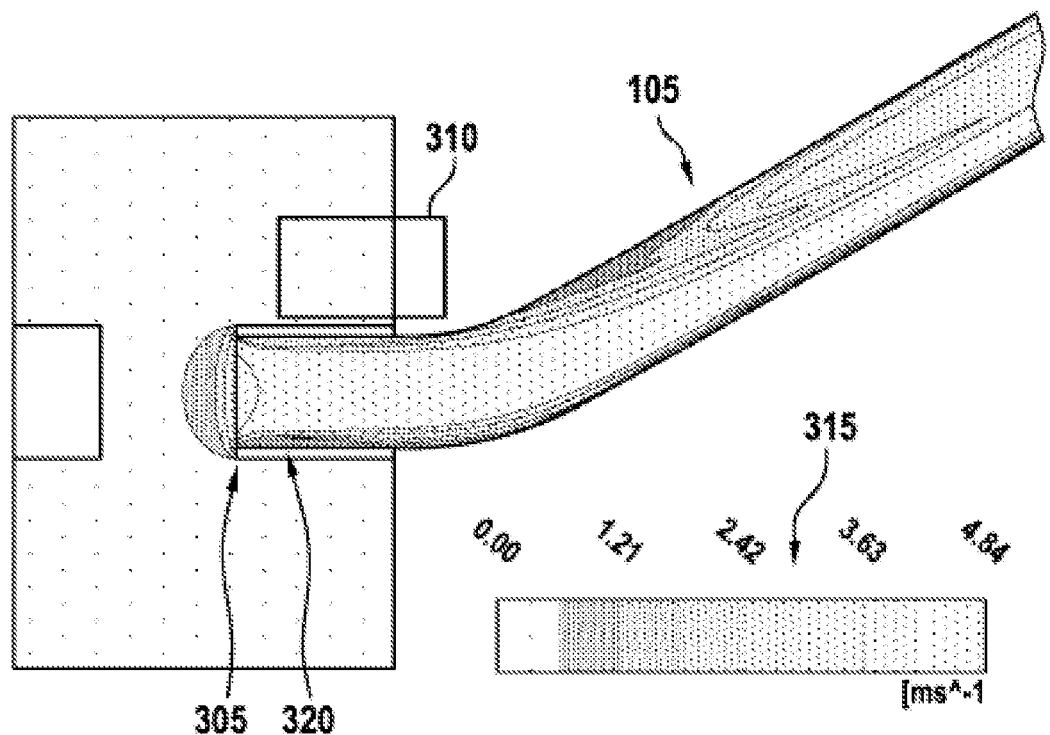
FIG. 3 a schematic illustration of a part of a feed line according to one design example.

FIG. 3 shows a schematic illustration of a part of a feed line 105 according to one design example. The figure shows a visualization of a flow separation 305 at an inlet edge in the inlet region 310 based on a flow velocity of a fluid flow conveyed through the feed line 105. The inlet region 310 shown here corresponds to a section of a portion of the feed line adjacent to the introduction opening. The scale 315 shows the flow velocity of the fluid flow. The flow separation 305 is also shown by the line 320, at which the flow velocity is equal to zero. The section in the inlet region 310 indicated by the line 320 can accordingly also be referred to as the "zero speed line". The flow separation 305 of the fluid flow shown here can be reduced using a design example of the inner surface contour and the contoured portion as described with reference to the preceding and following figures.

Figure 4:
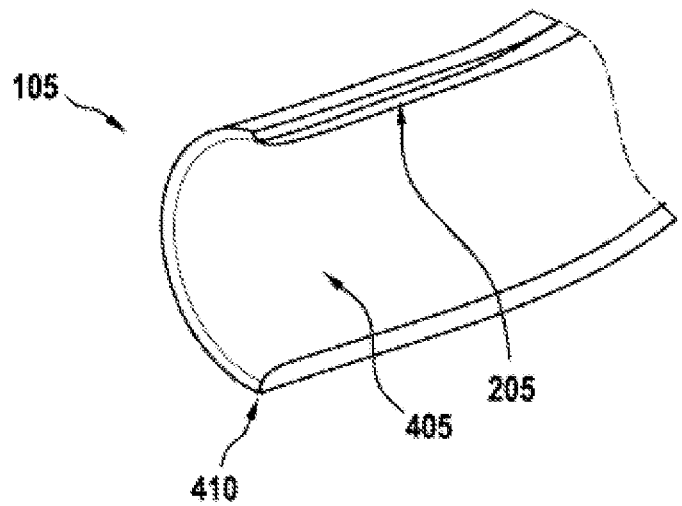
FIG. 4 a schematic illustration of a part of a feed line according to one design example.

FIG. 4 shows a schematic illustration of a part of a feed line 105 according to one design example. The figure shows a cross-section of the feed line 105, which is similar to or the same as the feed line described with reference to the preceding figures. FIG. 4 shows a configuration optimization in the inlet region of the feed line 105. The section of the feed line 105 shown here shows the inlet region 405 of the contoured portion adjacent to the introduction opening of the feed head portion. A region 410 adjacent to the inlet edge is rounded accordingly. The figure also shows the inner surface contour 205. In terms of reducing flow separation, the rounded portion in the region 410 and the configuration of the inner surface contour 205 can also be referred to as a local topology adaptation in the inlet region.

Figure 5:
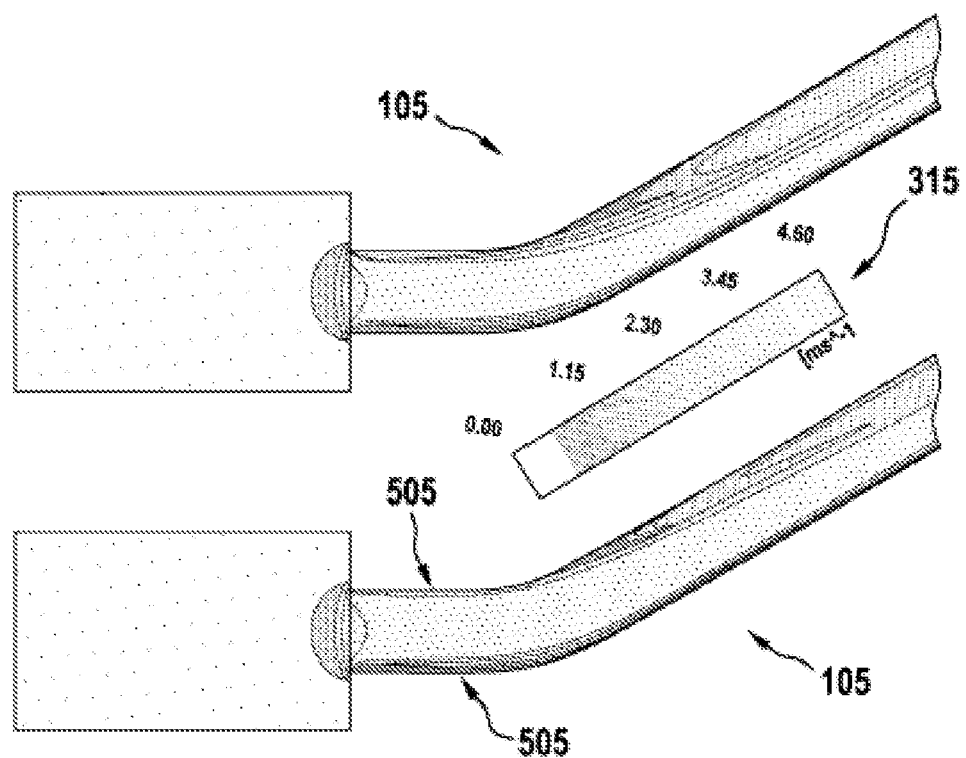
FIG. 5 a visualization of the effect of the implemented rounded portion in comparison to a hose with a constant inner diameter.

FIG. 5 shows a schematic illustration of a part of a feed line 105 according to one design example. The figure shows two scenarios of the flow behavior of the fluid flow on the basis of the flow separation in the feed line 105 which is detectable via the flow velocity. The scale 315 shows the flow velocity of the fluid flow. The feed line 105 at the top shows an example of the flow velocity of the fluid flow in a feed line 105 with flow separation in the inlet region, which can be detected with the aid of the "zero velocity lines" as described with reference to FIG. 3. The bottom feed line 105 scenario shows an example of the flow velocity of the fluid flow, in which flow separation in the inlet region is prevented as indicated with the label 505. The bottom scenario is similar or corresponds to the configuration of the contoured portion and the inner surface contour of the feed line 105 described with reference to FIG. 2.

Figure 6:
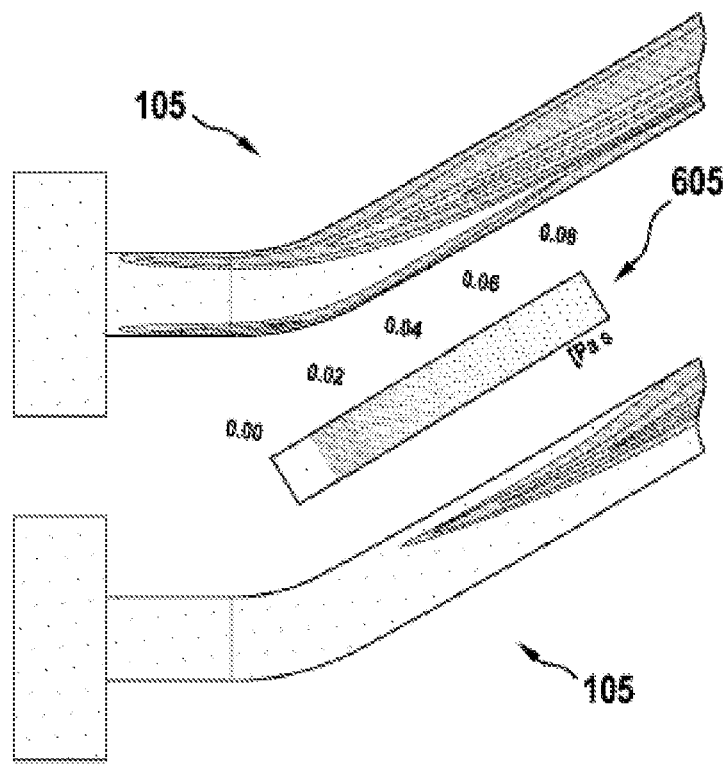
FIG. 6 a visualization of the effect of the implemented rounded portion in comparison to a hose with a constant inner diameter.

FIG. 6 shows a schematic illustration of a part of a feed line 105 according to one design example. The figure shows two scenarios of the flow behavior of the fluid flow based on the apparent viscosity of the turbulent flow, the eddy viscosity, which is visualized by the scale 605. The illustration of the viscosity of the turbulent flow also shows the friction of the fluid flow in the inlet region of the feed line 105. The feed line 105 at the top shows an example of the eddy viscosity of the fluid flow in a feed line 105 with flow separation in the inlet region. The bottom feed line 105 scenario shows an example of the reduction of the friction also in the region downstream of the inlet region of the feed line 105. The bottom scenario is similar or corresponds to the configuration of the contoured portion and the inner surface contour of the feed line 105 described with reference to FIG. 2.

Figure 7:
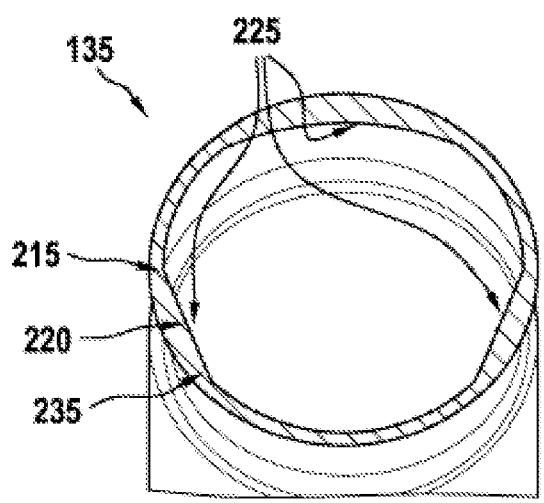
FIG. 7 a schematic illustration of part of a contoured portion of a feed line according to one design example.

FIG. 7 shows a schematic illustration of a part of a contoured portion 135 of a feed line according to one design example. The figure shows a cross-section of the contoured portion 135. The contoured portion 135 shown here is similar to or the same as the contoured portion as described with reference to FIG. 2. FIG. 7 also shows an example in which the rounded portion is not rotationally symmetrical.

Figure 8:
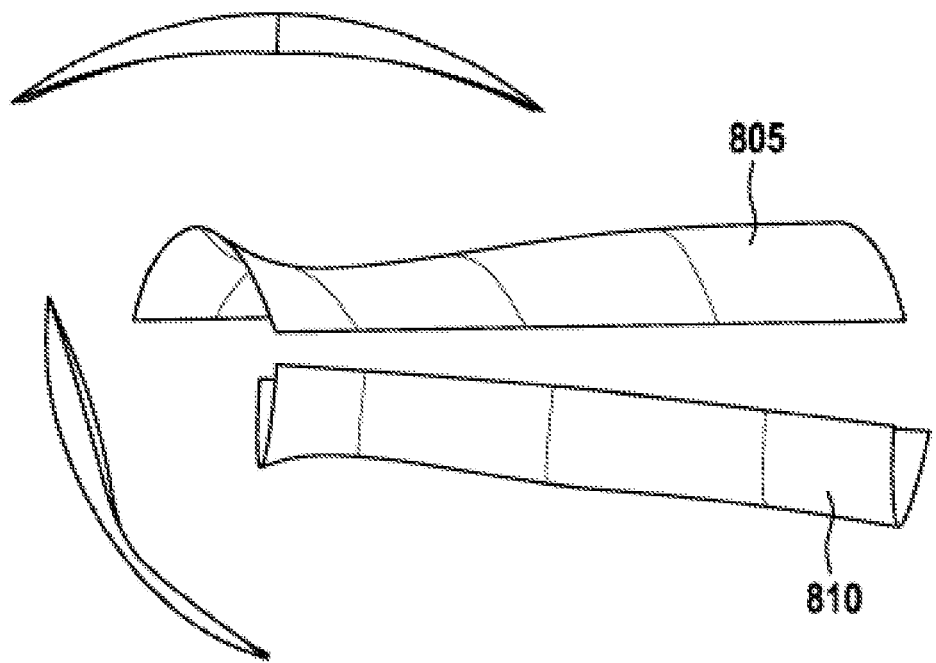
FIG. 8 a schematic illustration of part of an inner surface contour of a contoured portion of a feed line according to one design example.

FIG. 8 shows a schematic illustration of a part of an inner surface contour 205 of a contoured portion of a feed line according to one design example. According to the design example shown here, the inner surface contour 205 is configured as an insertion element of the contoured portion. As an example, the inner surface contour 205 here is configured as a two-part insertion element with two non-rotationally symmetrical inner surface contour parts 805, 810, which together form the inner surface contour 205 of the contoured portion. The two-part insertion element can be an example of the case, in which an inlet opening 140 has two open windows and one closed window. The illustration here shows different views of the inner surface contour 205 as an insertion element: The top view shows a cross-section through the inner surface contour part 805. The middle view shows the two inner surface contour parts 805 and 810 in a side view, and the bottom view shows a cross-section through the inner surface contour part 810. The inner surface contour parts 805 and 810 shown here individually or together form the inner surface contour 205 of the contoured portion of the feed line. They can therefore be referred to as a non-rotationally symmetrical optimization of the feed line for reducing flow separation.

Figure 9:
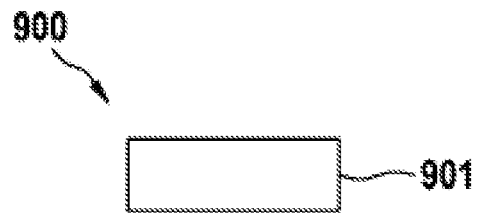
FIG. 9 a flow diagram of a method for producing a feed line for a cardiac support system according to one design example.

FIG. 9 shows a flow diagram of a method 900 for producing a feed line for a pump unit of a cardiac support system according to one design example. The feed line is configured to conduct a fluid flow to the pump unit of the cardiac support system. The method 900 includes a forming step 901. In the forming step 901, a feed head portion with at least one introduction opening for introducing the fluid flow into the feed line is formed. A contoured portion with an inner surface contour, wherein the contoured portion is disposed adjacent to the feed head portion is formed as well. An inner diameter of the contoured portion at a first position is greater than the inner diameter at a second position. The inner surface contour has a rounded portion at the second position for reducing the inner diameter.

In the forming step 901, the feed head portion and the contoured portion are cut out of a tube. Additionally or alternatively, the inner surface contour of the contoured portion is configured as an insertion element of the feed line.

The invention claimed is:

1. A cardiac support system, comprising:
   a pump unit; and
   a feed line configured to conduct a fluid flow to the pump unit, wherein the feed line comprises:
   a feed head portion comprising at least one introduction opening for receiving the fluid flow into the feed line; and
   a contoured portion disposed adjacent to the feed head portion and comprising an inner surface contour, wherein the inner surface contour comprises a first inner diameter at a first position, a second inner diameter at a second position, and a third inner diameter at a third position, wherein the first inner diameter is greater than the second inner diameter, wherein the third inner diameter is greater than the second inner diameter, wherein the first inner diameter comprises a maximum inner diameter of the contoured portion and the second inner diameter comprises a minimum inner diameter of the contoured portion, wherein the inner surface contour comprises a rounded portion at the second position, wherein the contoured portion comprises a first inner radius at the first position and a second inner radius at the second position, wherein the second inner radius is at most one fifth smaller than the first inner radius, and wherein the second position is located between the third position and the first position;

wherein:
the inner surface contour comprises an insertion element insertable within the feed line; and
a length of the insertion element is greater than a radius of the feed line up to twice an inner diameter of the contoured portion.

2. The cardiac support system according to claim 1, wherein the first position is located in the contoured portion between the feed head portion and the second position.

3. The cardiac support system according to claim 1, wherein an interior of the contoured portion is rotationally symmetrical about a central axis of the contoured portion.

4. The cardiac support system according to claim 1, wherein the contoured portion comprises a first wall thickness at the first position and a second wall thickness at the second position, wherein the first wall thickness is less than the second wall thickness.

5. The cardiac support system according to claim 1, wherein at least one inlet edge of the introduction opening of the feed head portion is rounded.

6. The cardiac support system according to claim 1, wherein the contoured portion comprises a constant outer diameter.

7. A method for producing a feed line for a pump unit of a cardiac support system, comprising:
forming a feed head portion with at least one introduction opening for receiving a fluid flow into the feed line, wherein the feed line is configured to conduct the fluid flow to the pump unit; and
forming a contoured portion adjacent to the feed head portion and comprising an inner surface contour, wherein the inner surface contour comprises a first inner diameter at a first position, a second inner diameter at a second position, and a third inner diameter at a third position, wherein the first inner diameter is greater than the second inner diameter, wherein the third inner diameter is greater than the second inner diameter, wherein the first inner diameter comprises a maximum inner diameter of the contoured portion and the second inner diameter comprises a minimum inner diameter of the contoured portion, wherein the inner surface contour comprises a rounded portion at the second position, wherein the contoured portion comprises a first inner radius at the first position and a second inner radius at the second position, wherein the second inner radius is at most one fifth smaller than the first inner radius, and wherein the second position is located between the third position and the first position;
wherein:
the inner surface contour comprises an insertion element insertable within the feed line; and
a length of the insertion element is greater than a radius of the feed line up to twice an inner diameter of the contoured portion.

8. The method according to claim 7, wherein the first position is located in the contoured portion between the feed head portion and the second position.

9. The method according to claim 7, wherein an interior of the contoured portion is rotationally symmetrical about a central axis of the contoured portion.

10. The method according to claim 7, wherein the contoured portion comprises a first wall thickness at the first position and a second wall thickness at the second position, wherein the first wall thickness is less than the second wall thickness.

11. The method according to claim 7, wherein at least one inlet edge of the introduction opening of the feed head portion is rounded.

12. The method according to claim 7, wherein the contoured portion comprises a constant outer diameter.

* * * * *